United States Patent [19]

Heckert et al.

[11] 4,005,119
[45] Jan. 25, 1977

[54] ORGANOSILANE COMPOUNDS

[75] Inventors: David C. Heckert, Oxford; David M. Watt, Jr., Cincinnati, both of Ohio;

[73] Assignee: The Proctor and Gamble Company, Cincinnati, Ohio

[22] Filed: Apr. 22, 1975

[21] Appl. No.: 570,539

[52] U.S. Cl. .................. 260/448.8 R; 260/448.2 N; 252/546; 252/548; 428/543

[51] Int. Cl.[2] ................... C07F 7/10; C07F 7/18

[58] Field of Search ............ 260/448.8 R, 448.2 N

[56] References Cited

UNITED STATES PATENTS

| | | | |
|---|---|---|---|
| 2,972,598 | 2/1961 | Morehouse | 260/448.8 R X |
| 3,389,160 | 6/1968 | Reid | 260/448.2 N |
| 3,471,541 | 10/1969 | Morehouse | 260/448.2 N X |
| 3,557,178 | 1/1971 | Golitz et al. | 260/448.8 R |
| 3,580,920 | 5/1971 | Culpepper | 260/448.8 R X |
| 3,624,120 | 11/1971 | Yetter | 260/448.2 N |
| 3,658,867 | 4/1972 | Prokai | 260/448.2 N |
| 3,661,963 | 5/1972 | Pepe et al. | 260/448.2 N |
| 3,817,739 | 6/1974 | Abbott et al. | 260/448.8 R X |
| 3,836,559 | 9/1974 | Prokai | 260/448.2 N |
| 3,898,257 | 8/1975 | Gregory | 260/448.8 R |

Primary Examiner—Paul F. Shaver
Attorney, Agent, or Firm—C. R. Wilson; R. B. Aylor; T. H. O'Flaherty

[57] ABSTRACT

Novel compounds of formula

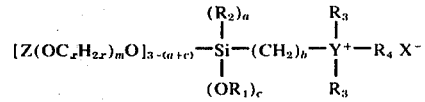

or siloxane oligomers thereof, wherein $x$ is 2 to 4, $m$ is 1 to 20, Z is hydrogen, an alkyl group containing 1 to 18 carbon atoms or an acyl group containing 1 to 4 carbon atoms, $a$ is 0 to 2; $c$ is 0 to 2 provided $a+c$ does not exceed 2; $R_1$ is an alkyl group containing 1 to 4 carbon atoms; $R_2$ is an alkyl group containing 1 to 18 carbon atoms; $b$ is 1 to 3; $R_3$ is an alkyl, aryl or arylalkyl group containing 1 to 12 carbon atoms, a caboxy-substituted alkyl group containing 1 to 4 carbon atoms,

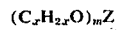

where $x$, $m$, and Z are as defined above, or oxygen provided only one $R_3$ is oxygen; $R_4$ is an alkyl, aryl, or arylalkyl group containing 1 to 22 carbon atoms; X is halide; and Y is nitrogen, phosphorus, or sulfur are disclosed. The novel compounds are useful for inclusion in a detergent composition for imparting soil release benefits to metallic and vitreous surfaces washed or rinsed therewith.

14 Claims, No Drawings

ORGANOSILANE COMPOUNDS

BACKGROUND OF THE INVENTION

This invention relates to novel organosilane compounds.

Various quaternized substituted organosilane compounds are known. For example, British Pat. No. 686,068 discloses compounds having the general formula

where R is an alkyl, monocyclic aryl hydrocarbon or alkoxy radical, $R^1$ is an alkyl, alicyclic hydrocarbon or monocyclic aryl hydrocarbon radical or hydroxy alkyl radical, $a$ is 1 to 2, $b$ is 0 to 3 with $a+b$ being not greater than 4 and Y is an acid anion. British Pat. No. 1,164,581 discloses compounds of the general formula

wherein R is an alkyl radical containing 1 to 6 carbon atoms or a phenyl radical and $a$ is 1 or 2. U.S. Pat. No. 3,730,701 discloses compounds of the formula

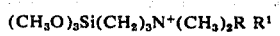

where R is an alkyl group containing 11 to 22 carbon atoms, and $R^1$ is halide. These compounds are said to be useful as intermediates in the formation of organosilicon resins, catalysts and emulsifying agents (British Pat. No. 686,068), interfacial active agents and as modifiers for organopolysiloxane resins and oils (British Pat. No. 1,164,581) and for the control of algae (U.S. Pat. No. 3,730,701).

U.S. Pat. No. 2,955,127 discloses compounds of formula

where R is a monovalent hydrocarbon group, $a$ is at least 2, and Z is a monovalent hydrocarbon group, an alkoxy group, aryloxy group, hydroxy group, siloxy group or a

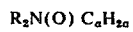

group.

It has now been found that the novel compounds as hereindescribed are useful as an additive to a detergent composition. Commonly assigned copending Patent Applications "Organosilane-Containing Detergent Composition" and "Organosilane-Containing Anionic Detergent Compositions", both by Heckert and Watt, filed of even date, U.S. Ser. Nos. 570,534 and 576,533 respectively disclose detergent compositions containing a class of organosilanes. When metallic or vitreous surfaces are washed with a detergent composition containing the organosilane, a thin polymeric coating of the organosilane is deposited upon the washed or rinsed surfaces. The polymerized coating imparts a soil release benefit to the surface, thereby making the surface easier to clean in subsequent washings.

It is an object of this invention to produce novel organosilane compounds.

It is another object of this invention to produce organosilane compounds having utility in a detergent composition.

These and other objects will become apparent from the description to follow.

As used herein all percentages and ratios are by weight unless otherwise indicated.

SUMMARY OF THE INVENTION

An organosilane having the formula

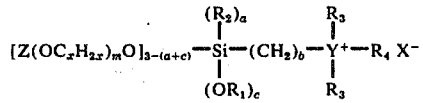

or siloxane oligomers thereof, wherein $x$ is 2 to 4, $m$ is 1 to 20, Z is hydrogen, an alkyl group containing 1 to 18 carbon atoms or an acyl group containing 1 to 4 carbon atoms; $a$ is 0 to 2; $c$ is 0 to 2 provided $a+c$ does not exceed 2; $R_1$ is an alkyl group containing 1 to 4 carbon atoms; $R_2$ is an alkyl group containing 1 to 18 carbon atoms; $b$ is 1 to 3; $R_3$ is an alkyl, aryl or arylalkyl group containing 1 to 12 carbon atoms, a carboxy-substituted alkyl group containing 1 to 4 carbon atoms,

where $x$, $m$, and Z are as defined above, or oxygen provided only one $R_3$ is oxygen; $R_4$ is an alkyl, aryl, or arylalkyl group containing 1 to 22 carbon atoms; X is halide; and Y is nitrogen, phosphorus, or sulfur.

DETAILED DESCRIPTION OF THE INVENTION

This invention relates to organosilane compounds having the formula

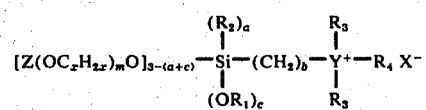

or siloxane oligomers thereof wherein Z, $x$, $m$, $a$, $c$, $R_1$, $R_2$, $b$, $R_3$, $R_4$, Y and X are as defined immediately above. Preferably X is chloride or bromide, $(a+c)$ is 2, $R_2$ is a methyl group, $R_3$ is an alkyl group containing 1 to 4 carbon atoms and $R_4$ is an alkyl, aryl or arylalkyl group containing 6 to 12 carbon atoms.

It should be understood that $R_3$ in the above formula and formulas to follow may be the same or different. It should be further understood that when Y is sulfur, there will be only one $R_3$. The 1 to 4 carbon atoms in the carboxy-substituted alkyl group is inclusive of the carboxyl group. Also, when one $R_3$ is oxygen or, under basic conditions, the anion of a carboxylic acid substituted alkyl, the counter ion $X^-$ is not extant.

Compounds of the formula

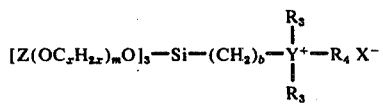

wherein $b$ is 3, $R_3$ is an alkyl, aryl or arylalkyl group, and Z, $x$, $m$, $R_4$, Y and X are defined as above are prepared by the following route:

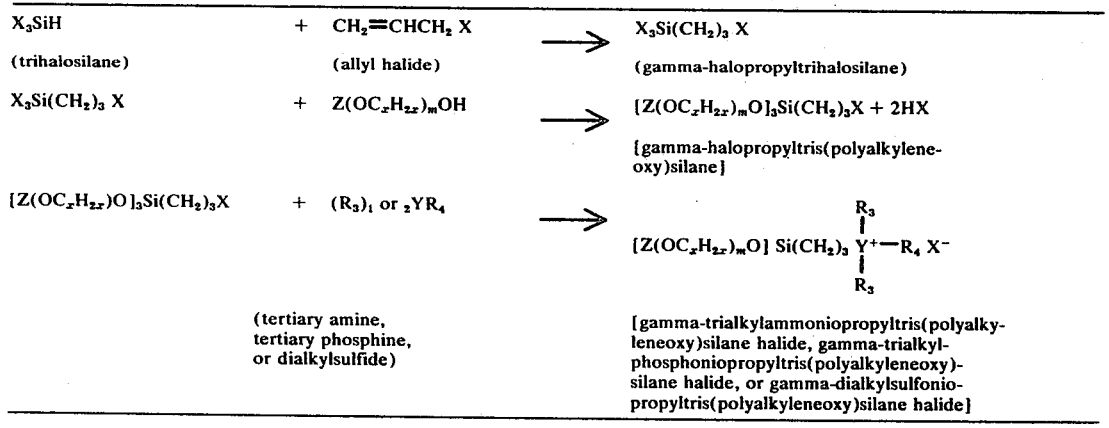

The trihalosilane (where the halogen is chloride or bromide) is reacted with the allyl chloride at about 100° C. for from 4 to 10 hours in the presence of a catalyst, e.g., chloroplatinic acid or platinum. The resultant gammahalopropyltrihalosilane is reacted with a $Z(OC_xH_{2x})_mOH$ compound to produce the gamma-halopropyltris(-polyalkyleneoxy)silane. At least three equivalents of the $Z(OC_xH_{2x})_mOH$ per equivalent of halo-propyltrihalosilane are added slowly to the silane. The gamma-halopropyltrihalosilane may be dissolved in an inert solvent, preferably hexane or pentane. (See W. Noll, "Chemistry and Technology of Silanes", Academic Press, New York, 1968, page 81 for the alcoholysis of halosilanes.) One equivalent of the gamma-halopropyltris(polyalkyleneoxy)silane is reacted with one equivalent of the tertiary amine, tertiary phosphine, or dialkylsulfide to produce the organosilane. An inert solvent, preferably of high dielectric constant, may be used. The reaction is carried out at temperatures of from 40° to 100° C. and a time of 2 to 10 hours for the reaction of the bromopropyltris(polyalkyleneoxy)silane and 120° to 140° C. for 2 to 20 hours for the reaction of the chloropropyltris(polyalkyleneoxy)silane.

The compounds of Formula I when at least one $R_4$ is a carboxy-substituted alkyl group are prepared in the same manner except for the last reaction step. Here, a tertiary amine, tertiary phosphine or dialkylsulfide having a carboxy-containing alkyl group(s) is reacted with the alpha, beta or gamma-haloalkyltris(polyalkyleneoxy)silane at 50° C. to 200° C. for 2 hours to 20 hours. Such carboxy-substituted tertiary amines, tertiary phosphines, and dialkylsulfides are produced by reacting $R_3YHR_4$ or $HYR_4$ (where Y is sulfur)

with $X(CH_2)_{1-3}COOH$ in the presence of base at elevated temperatures, e.g. 50° to 150° C.

The compounds of Formula I when at least one $R_4$ is $(C_xH_{2x}O)_mZ$ with x, m and Z as defined above are produced in the manner given above except for the last reaction. Thus, alpha-beta- and gamma-haloalkyltris(polyalkyleneoxy)silane is reacted with a tertiary amine, tertiary phosphine, or dialkylsulfide where at least one substituent is $(C_xH_{2x}O)_mZ$ The reaction takes place at a temperature of 50° to 200° C. and a time of from 2 to 10 hours.

Compounds of Formula I when one $R_4$ is oxygen are prepared by following the reactions outlined above up to the last reaction step. At this point, a dialkyl amine, dialkyl phosphine or alkylthiol is reacted with the halosilane at 50° to 200° C. for from 4 to 10 hours and then with base to produce an intermediate tertiary amine, phosphine, or dialkyl sulfide. These intermediates are then reacted with $H_2O_2$ at 20° C. to 100° C. or preferably $O_3$ in an inert solvent at $-80°$ C. to 20° C. to yield the organosilane.

When b is 2 in Formula I, a trihalovinylsilane of formula $X_3SiCH=CH_2$ (which is commercially available) is reacted with hydrogen bromide in the presence of peroxide and light to produce a beta-haloethyltrihalosilane. This compound is reacted with $Z(OC_xH_{2x})_mOH$ and thereafter with an appropriate amine, phosphine, of sulfide in the manner discussed above for the preparation of the compounds of Formula I when b is 3.

When b is 1 in Formula I, the starting reactant is a commercially available trihalomethylsilane of formula $X_3SiCH_3$.

This silane is reacted with chlorine or, preferably a half mole of bromine and a half mole of chlorine in the presence of light (such as provided by an ordinary tungsten or fluorescent lamp). The resultant alpha-halomethyltrihalosilane is reacted with $Z(OC_xH_{2x})_mOH$ and thereafter an appropriate amine, phosphine or sulfide in the manner discussed above with the compounds of Formula I when $b$ is 3.

When $a$ is 1 or 2 and $c$ is 0, the organosilane is prepared in a manner similar to the preparation of the compounds of Formula I except for the fact that the starting reactants (when $b$ is 1, 2, or 3) all have a $C_{1-18}$ alkyl group or two $C_{1-18}$ alkyl groups attached to the Si atom in place of a halogen atom(s). The starting reactant is commercially available when $R_2$ is $CH_3$. When $R_2$ is $C_2H_5$ or greater, the compound is prepared by reacting a silane with an appropriate olefin. Thus, $$X_{3-a}SiH_{1+a}$$

is reacted with a $C_2$ to $C_{18}$ olefin to obtain the desired starting reactant. The remaining reaction steps and conditions for producing the desired organosilane are essentially the same as for producing the compounds of Formula I.

When $a$ is 0 or 1 and $c$ is 1 or 2 the organosilane is formed in substantially the same manner as those of Formula I except that a mixture of $R_1OH$ and $$Z(OC_xH_{2x})_mOH$$

in the desired ratio is used in place of the $$Z(OC_xH_{2x})_mOH$$

in the reaction with the haloalkyltrihalosilane.

Alternatively, the subject compounds are formed by reacting 3 equivalents of $R_1OH$ with the haloalkyltrihalosilane and reacting the resultant compound with the amine, phosphine or sulfide to produce an organosilane having three $R_1O$ groups attached to the silicon atoms. This compound is then heated with less than 3-a equivalents of $$(OC_xH_{2x})_mOH$$

under conditions such that $R_1OH$ is removed from the system.

Exemplary compounds follow:
[Ch$_3$(OC$_2$H$_4$)O]$_3$SiCH$_2$N$^+$(CH$_3$)$_2$C$_{14}$H$_{29}$ Cl$^-$
[CH$_3$(OC$_2$H$_4$)$_5$O]$_2$CH$_3$Si(CH$_2$)$_3$N$^+$(CH$_2$COOH)$_2$C$_{10}$H$_{21}$ Cl$^-$
[H(OC$_3$H$_6$)$_3$O]$_3$SiCH$_2$N$^+$(C$_2$H$_4$OH) (C$_3$) C$_{12}$H$_{25}$) Cl$^-$
[H(OC$_2$H$_4$)$_{18}$O]$_3$Si(CH$_2$)$_2$N$^+$(O)$^-$(CH$_3$)C$_{18}$H$_{37}$
[CH$_3$CO(OC$_2$H$_4$)$_{10}$O]$_3$SiCH$_2$N$^+$[(C$_2$H$_4$O)$_{14}$H]$_2$C$_8$H$_{16}$C$_6$H$_5$ Cl$^-$
[C$_{16}$H$_{33}$(OC$_2$H$_4$)$_8$O]$_2$C$_6$H$_{13}$SiCH$_2$N$^+$[C$_3$H$_6$O)CH$_3$](CH$_3$)$_2$ Br$^-$
[H(OC$_4$H$_8$)$_8$O]$_3$SiCH$_2$N$^+$[(C$_2$H$_4$O)$_4$COCH$_3$]$_2$CH$_3$ Cl$^-$
[C$_6$H$_{13}$(OC$_2$H$_4$)$_2$O]$_3$Si(CH$_2$)$_2$P$^+$(CH$_3$)$_2$C$_{10}$H$_{21}$ Br$^-$
[CH$_3$(OC$_3$H$_6$)$_{14}$O]$_3$SiCH$_2$P$^+$(C$_2$H$_4$COOH) (C$_6$H$_{13}$)$_2$Cl$^-$
[C$_2$H$_5$(OC$_2$H$_4$)O]$_3$CH$_3$Si(CH$_2$)$_2$P$^+$(C$_4$H$_8$OH) (CH$_3$)C$_6$H$_5$ Cl$^-$
[CH$_3$(OC$_2$H$_4$)$_8$O]$_3$SiCH$_2$P$^+$(O)$^-$(CH$_3$)C$_8$H$_{17}$
[C$_2$H$_5$OC(OC$_2$H$_4$)$_2$O]$_3$Si(CH$_2$)$_3$P$^+$[C$_2$H$_4$O)$_6$H]$_2$C$_6$H$_{13}$ Cl$^-$
[CH$_3$(OC$_4$H$_8$)O]$_3$SiCH$_2$P$^+$[(C$_3$H$_6$O)$_2$C$_7$H$_{15}$](C$_4$H$_9$)$_2$ Br$^-$
[C$_2$H$_5$OC(OC$_2$H$_4$)O]$_3$SiCH$_2$S$^+$(CH$_3$)C$_{18}$H$_{37}$ Cl$^-$
[H(OC$_2$H$_4$)$_4$O]$_3$Si(CH$_2$)$_2$S$^+$(C$_2$H$_4$COOH)C$_{12}$H$_{25}$ Br$^-$
[H(OC$_2$H$_4$)$_5$O](CH$_3$)(C$_2$H$_5$O)SiCH$_2$N$^+$(CH$_3$)$_2$C$_{12}$H$_{25}$ Cl$^-$
[C$_{12}$H$_{25}$(OC$_2$H$_4$)$_3$O](CH$_3$O)$_2$Si(CH$_2$)$_3$N$^+$(C$_2$H$_5$)$_2$C$_6$H$_5$ Cl$^-$
[H(OC$_4$H$_8$)$_6$O](C$_2$H$_5$O)$_2$Si(CH$_2$)$_3$N$^+$[(C$_2$H$_4$O)$_{10}$H]$_2$C$_{18}$H$_{37}$ Br$^-$
[CH$_3$CO(OC$_2$H$_4$)$_3$O]$_2$(C$_2$H$_5$O)Si(CH$_2$)$_2$N$^+$[(C$_2$H$_4$O)C$_2$H$_5$](C$_6$H$_5$CH$_3$)$_2$ Cl$^-$
[H(OC$_2$H$_4$)$_{12}$O](C$_4$H$_8$O)$_2$SiCH$_2$N$^+$[(C$_2$H$_4$O)$_4$COCH$_3$]$_2$C$_{14}$H$_{29}$ Cl$^-$
[C$_{16}$H$_{33}$(OC$_2$H$_4$)$_3$O](C$_2$H$_5$) (CH$_3$O)SiCH$_2$N$^+$(-0)$^-$(CH$_3$)C$_6$H$_{13}$
[H(OC$_3$H$_6$)$_{12}$O](C$_2$H$_5$O)$_2$SiCH$_2$N$^+$(C$_2$H$_5$COOH) (CH$_3$)C$_{10}$H$_{21}$ Cl$^-$
[C$_2$H$_5$(OC$_2$H$_4$)$_{14}$O]$_2$(C$_4$H$_9$O)Si(CH$_2$)$_3$N$^+$(C$_4$H$_8$ OH) (CH$_3$)C$_{14}$H$_{29}$ Cl$^-$
[H(OC$_2$H$_4$)$_{16}$O]$_2$(CH$_3$O)SiCH$_2$P$^+$(CH$_3$)$_2$C$_6$H$_4$C$_2$H$_5$ Cl$^-$
[C$_3$H$_7$(OC$_2$H$_4$)$_6$O](C$_2$H$_5$) (CH$_3$O)SiCH$_2$P$^+$[(C$_2$H$_4$O)$_8$H]$_2$C$_8$H$_{17}$ Br$^-$
[CH$_3$OC(OC$_2$H$_4$)$_2$O]$_2$(CH$_3$O)Si(CH$_2$)$_2$P$^+$[(C$_3$H$_6$O)$_3$C$_2$H$_5$](C$_4$H$_9$)$_2$ Cl$^-$
[H(OC$_4$H$_8$)$_2$O](C$_{12}$H$_{25}$) (CH$_3$O)SiCH$_2$P$^+$(O)$^-$(CH$_3$)C$_6$H$_5$ $_2$
[C$_{14}$H$_{29}$(OC$_2$H$_4$)$_6$O](CH$_3$O)$_2$SiCH$_2$P$^+$(C$_3$H$_6$COOH)$_2$CH$_3$ Cl$^-$
[H(OC$_2$H$_4$)$_8$O]$_2$(C$_4$H$_9$O)SiCH$_2$P$^+$(C$_3$H$_6$ OH)$_2$C$_2$H$_5$ Br$^-$
[H (OC$_2$H$_4$)$_{10}$O]$_2$(C$_3$H$_7$O)SiCH$_2$S$^+$(CH$_3$)C$_6$H$_{12}$C$_6$H$_5$ Cl$^-$
[CH$_3$(OC$_2$H$_4$)$_{20}$O]$_3$Si(CH$_2$)$_3$S$^+$(C$_3$H$_6$OH)C$_{16}$H$_{33}$ Br$^-$
[H(OC$_3$H$_6$)$_{12}$O]$_3$Si(CH$_2$)$_2$S$^+$(O)$^-$C$_5$H$_{11}$
[C$_{12}$H$_{25}$(OC$_2$H$_4$)$_4$O]$_3$SiCH$_2$S$^+$[(C$_2$H$_4$O)$_{20}$H]CH$_3$ Br$^-$
[H(OC$_2$H$_4$)$_{12}$O]$_3$Si(CH$_2$)$_3$S$^+$[(C$_2$H$_4$O)C$_{14}$H$_{29}$]C$_6$H$_4$CH$_3$ Cl$^-$
[H(OC$_4$H$_8$)$_2$O]$_2$(CH$_3$O)Si(CH$_2$)$_3$S$^+$[(C$_2$H$_4$O)$_4$H]CH$_3$ Br$^-$
[C$_{12}$H$_{25}$(OC$_2$H$_4$)$_6$O](CH$_3$)(CH$_3$O)SiCH$_2$S$^+$[(C$_3$H$_6$O)$_8$CH$_3$]C$_3$H$_7$ Cl$^-$
[CH$_3$CO(OC$_2$H$_4$)$_3$O](C$_2$H$_5$O)$_2$Si(CH$_2$)$_2$S$^+$(C$_2$H$_4$OH)C$_{12}$H$_{25}$ Cl$^-$
[CH$_3$(OC$_3$H$_6$)$_{12}$O](CH$_3$O)$_2$SiCH$_2$S$^+$(C$_3$H$_6$COOH)CH$_2$C$_6$H$_5$ Br$^-$
[H(C$_2$H$_4$O)$_6$O](C$_{12}$H$_{25}$)(CH$_3$O)SiCH$_2$S$^+$(O)$^-$C$_{14}$H$_{29}$ Siloxane oligomers of the organosilanes are formed from the monomers by the controlled addition of from 1 to 100 equivalents of water, preferably in an inert solvent such as alcohol, tetrahydrofuran, etc. As used herein, "oligomers" is used to mean a degree of polymerization of from 2 to 100, preferably 2 to 20. A higher degree of polymerization adversely affects the ability of the compound to bond itself to a metallic or vitreous surface as discussed below and is for this reason avoided. Examples of siloxane oligomers having varying degrees of polymerization are readily visualized from the above examples of organosilane monomers.

The above organosilanes are useful when used in a detergent composition at a level of organosilane to watersoluble organic detergent of from 2:1 to 1:10,000. When metallic or vitreous surfaces are washed or rinsed with a detergent composition containing the above-described organosilane, a soil release benefit is imparted to the surface. It is theorized that the positively charged organosilane is attracted to the negatively charged surface. The silicon atom in the organosilane can then form a bond with the surface. The presence of the positive charge on the organosilane is necessary to allow the bonding to take place from a dilute solution as is normally encountered with detergent compositions and within a reasonable time period. The terminal alkyl groups attached to the positively charged atom provides the soil release benefits. It is believed that the organosilane compound polymerizes on the surface to form a thin coating of the polymer.

The coating is responsible for imparting the soil release benefits to the surface. That is, a hard surface having on it the polymeric coating will be soiled; however, the soil is not tenaciously bound to the surface by virtue of the coating and for this reason is easily washed away.

The following examples illustrate the invention.

EXAMPLE I

$(CH_2CH_2COO^-)C_{18}H_{37}$

A mixture of 12.0g of gamma-bromopropyltrimethoxysilane and 14.15g of octadecylmethylamine are heated at 94-113° C. for 16 hours and then cooled. The resulting tertiary ammonium salt is dissolved in 100 ml of absolute ethanol and 0.05 moles of freshly prepared sodium ethoxide in 50 ml of ethanol is added. Filtration of the resulting solution and removal of the solvent yield the tertiary amine, gammamethyloctadecylaminopropyltrimethoxysilane.

A mixture of 22.2g (0.05 mole) of this product and 8.75g of

are heated in 78g of methyl carbitol for 18 hr at 130° C. NMR analysis of the resulting product indicates complete reaction yielding the expected zwitterionic silane wherein part of the methoxy on silicon is displaced by a methylcarbitol moiety.

Corresponding organosilanes wherein the nitrogen atom is replaced by a phosphorous atom or a sulfur atom are produced by the above reaction steps by using octadecylmethylphosphine or octadecylsulfide in place of the octadecylmethylamine.

EXAMPLE II

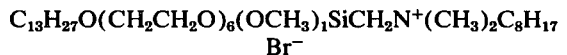

A mixture of 20g (0.1 mole) of methylbromomethyldimethoxysilane, 15.7g of octydimethylamine, 46.4g of coconut alcohol ethoxylated with 6 moles of ethylene oxide, and 100 ml. of 2-butanone are refluxed for 12 hours. The 2-butonone is then distilled out of the mixture at atmospheric pressure along with 0.1 moles of methanol to leave the desired product.

EXAMPLE III

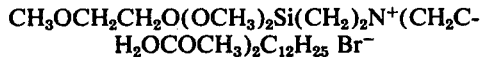

To 161.5g of vinyltrichlorosilane (commercially available) in 300 ml. of hexane is added an excess of dry HBr. The reaction flask is sealed and kept for 24 hours, whereupon it is opened and the product is stripped and distilled yielding beta-bromoethyltrichlorosilane.

One-half mole of the beta-bromoethyltrichlorosilane is dissolved in 100 ml. of dry hexane and 0.5 moles of betamethoxyethanol is added dropwise while the solution is agitated by a nitrogen flush. One hour after completion of the addition, 1.2 moles of methanol is added continuing the nitrogen flush. After all HCl evolution has ceased, the residue is distilled yielding

Two-tenths mole (54.6g) of this product and two-tenths mole (72g) of the diacetate of dodecyldiethanolamine are mixed with 200 ml. of acetonitrile and refluxed for 12 hours. Removal of the acetonitrile under reduced pressure yields the desired product.

What is claimed is:

1. An organosilane having the formula

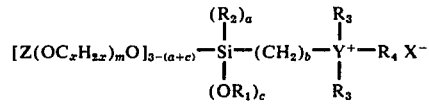

or siloxane oligomers thereof, wherein $x$ is 2 to 4, $m$ is 1 to 20, Z is hydrogen, an alkyl group containing 1 to 18 carbon atoms or an acyl group containing 1 to 4 carbon atoms; $a$ is 0 to 2; $c$ is 0 to 2 provided a+c does not exceed 2; $R_1$ is an alkyl group containing 1 to 4 carbon atoms; $R_2$ is an alkyl group containing 1 to 18 carbon atoms, $b$ is 1 to 3; $R_3$ is an alkyl, aryl or arylalkyl group containing 1 to 12 carbon atoms, a carboxy-substituted alkyl group containing 1 to 4 carbon atoms,

where $x$, $m$, and Z are as defined above, or oxygen provided only one $R_3$ is oxygen and further provided that when $R_3$ is oxygen there is no $X^-$; $R_4$ is an alkyl, aryl, or arylalkyl group containing 1 to 22 carbon atoms; X is halide; and Y is nitrogen, phosphorus, or sulfur.

2. The organosilane of claim 1 wherein $(a+c)$ is 2.

3. The organosilane of claim 1 where $c$ is 1 or 2.

4. The organosilane of claim 1 wherein the siloxane oligomer has a degree of polymerization of from 2 to 100.

5. The organosilane of claim 1 wherein the degree of polymerization is from 2 to 20.

6. The organosilane of claim 1 wherein the organosilane is a monomer.

7. The organosilane of claim 1 wherein Z is hydrogen.

8. The organosilane of claim 1 wherein Z is an alkyl group.

9. The organosilane of claim 1 wherein Z is an acyl group.

10. The organosilane of claim 1 wherein X is chloride or bromide.

11. The organosilane of claim 1 wherein $R_2$ is methyl.

12. The organosilane of claim 1 wherein $R_3$ is an alkyl group containing 1 to 4 carbon atoms.

13. The organosilane of claim 1 wherein $R_4$ contains 6 to 12 carbon atoms.

14. The organosilane of claim 1 having the formula

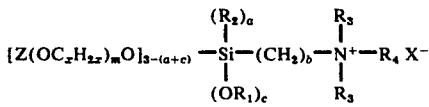

or siloxane oligomers thereof, wherein $x$ is 2 to 4, $m$ is 1 to 20, Z is hydrogen, or alkyl group containing 1 to 18 carbon atoms or an acyl group containing 1 to 4 carbon atoms, $R_1$ is an alkyl group containing 1 to 4 carbon atoms; $a$ is 0 to 2; $c$ is 0 to 2 provided a+c does not exceed 2; $R_2$ is an alkyl group containing 1 to 18 carbon atoms; $b$ is 1 to 3; $R_3$ is an alkyl, aryl, or arylalkyl group containing 1 to 12 carbon atoms, a carboxy-substituted alkyl group containing 1 to 4 carbon atoms, $(C_xH_{2x}O)_mZ$ wherein $x$, $m$, and Z are as defined above, or oxygen provided only one $R_3$ is oxygen and further provided that when $R_3$ is oxygen there is no $X^-$; $R_4$ is an alkyl, aryl or arylalkyl group containing 1 to 22 carbon atoms; and X is halide.

* * * * *